United States Patent [19]

Burow, Jr.

[11] 4,322,429

[45] Mar. 30, 1982

[54] ISOXAZOLYLBENZAMIDES AS INSECTICIDES

[75] Inventor: Kenneth W. Burow, Jr., Indianapolis, Ind.

[73] Assignee: Eli Lilly and Company, Indianapolis, Ind.

[21] Appl. No.: 187,677

[22] Filed: Sep. 16, 1980

[51] Int. Cl.³ .................. A01N 43/80; C07D 261/14; C07D 261/20
[52] U.S. Cl. .................................. 424/272; 548/241; 548/245; 548/246
[58] Field of Search ...................... 548/241, 245, 246; 424/272

[56] References Cited

U.S. PATENT DOCUMENTS 3,360,516 12/1967 Harris et al. ..................... 260/256.4

FOREIGN PATENT DOCUMENTS

| | | |
|---|---|---|
| 6936760 | 8/1971 | France . |
| 7015233 | 12/1971 | France . |
| 53-86033 | 7/1978 | Japan . |
| 54-59272 | 5/1979 | Japan . |
| 1157586 | 7/1969 | United Kingdom . |

OTHER PUBLICATIONS

Derwent Abstract of Japanese 54052075, 9/1977.

*Primary Examiner*—Anton H. Sutto
*Attorney, Agent, or Firm*—Gerald V. Dahling; Arthur R. Whale

[57] ABSTRACT

The present invention is directed to isoxazolyl and benzisoxazolyl benzamide compounds useful as insecticides.

162 Claims, No Drawings

ISOXAZOLYLBENZAMIDES AS INSECTICIDES

The present invention is directed to novel compounds of the formula

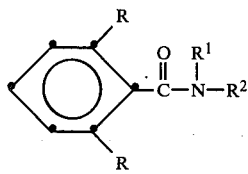

wherein each R is selected from the group consisting of
H,
F,
Br,
Cl,
$CH_3$, or
$OCH_3$,
with the proviso that each R cannot simultaneously represent H;
$R^1$=H, $C_1$–$C_3$ alkyl, or 2,6-dichlorobenzoyl, subject to the proviso that when $R^1$=2,6-dichlorobenzoyl, both R groups simultaneously represent chloro;
$R^2$=a 3-isoxazolyl of the formula

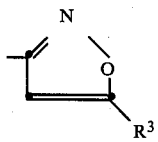

with the proviso that each R cannot simultaneously represent methyl or methoxy, and subject to the further proviso that when one R represents methyl the other R cannot simultaneously represent methoxy, wherein
$R^3$=unsubstituted phenyl, 3,4-dihalophenyl, or a meta- or para-substituted phenyl of which the substituent is Br, Cl, F, I, $C_1$–$C_3$ alkyl, $O_mC_nF_{2n+1}$, $O_mC_nF_{2n}H$, $\phi$, or -$O\phi$, m=0-1 and n independently=1-2 with the proviso that when $R^1$ represents 2,6-dichlorobenzoyl, $R^3$ cannot represent unsubstituted phenyl, or meta- or para-(trifluoromethyl)phenyl; or
$R^2$=a 5-isoxazolyl of the formula

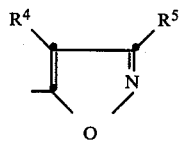

with the proviso that $R^1$=H, and subject to the further proviso that when one R represents $CH_3$ or $OCH_3$ the other R cannot simultaneously represent halo, wherein
$R^4$=H, or para-(trifluoromethyl)phenyl;
$R^5$=H, para-chlorophenyl, or an ortho- or meta-substituted phenyl of which the substitutent is Cl, $CH_3$, or $CF_3$ with the proviso that
(a) when $R^5$ is para-chlorophenyl, neither R can represent H,
(b) when $R^5$ is meta-(trifluoromethyl)-phenyl, each R cannot simultaneously represent an $OCH_3$ moiety,
(c) $R^4$ and $R^5$ cannot simultaneously represent H,
(d) when $R^4$ represents para-(trifluoromethyl)phenyl, $R^5$ represents H; or
$R^2$=a 3-benzisoxazolyl of the formula

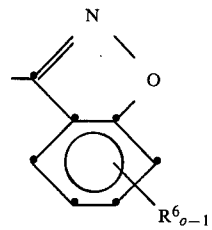

subject to the proviso that $R^1$=H, and subject to the further proviso that each R cannot simultaneously represent methyl or methoxy and when one R represents methyl the other R cannot simultaneously represent methoxy, wherein
$R^6$=halo, $C_1$–$C_3$ alkyl, $O_mC_nF_{2n+1}$, or $O_mC_nF_{2n}H$, m=0-1 and n independently=1-2;
or in the case of $R^1$=$C_1$–$C_3$ alkyl and each R simultaneously=chloro, the endo-alkylated and endo-acylated isoxazole tautomers thereof.

The present invention is also directed to methods employing and compositions comprising the above compounds as insecticides.

DETAILED DESCRIPTION OF THE INVENTION

For purposes of the present application, the compounds of this invention are named as substituted benzamides. Therefore the compounds are named, in the case of $R^2$=a 3-isoxazolyl, as 2-substituted or 2,6-disubstituted-N-(5-substituted-3-isoxazolyl)benzamides or, in the case of $R^1$=2,6-dichlorobenzoyl or $C_1$–$C_3$ alkyl, as 2-substituted or 2,6-disubstituted-N-2,6-dichlorobenzoyl or $C_1$–$C_3$ alkyl-N-(5-substituted-3-isoxazolyl)benzamides, or in the case of $R^2$=a 5-isoxazolyl, as 2-substituted or 2,6-disubstituted-N-(3- or 4-substituted-5-isoxazolyl)benzamides, or in the case of $R^2$=a benzisoxazolyl, as 2-substituted or 2,6-disubstituted-N-(substituted or non-substituted-3-benzisoxazolyl)benzamides.

The compounds of the present invention are readily prepared by the reaction of a benzoylchloride of the formula

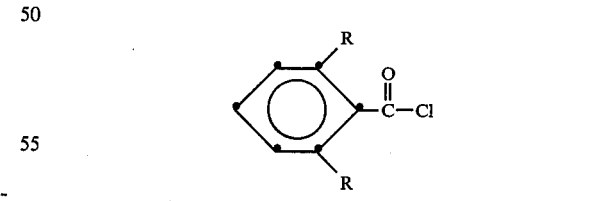

with a 3-aminoisoxazole of the formula

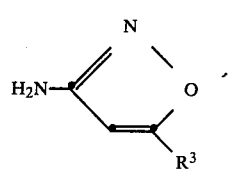

or with a 5-aminoisoxazole of the formula

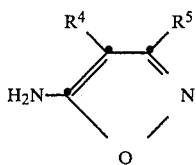

or with a 3-aminobenzisoxazole of the formula

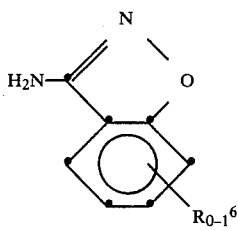

The reaction is well known in the art and is conveniently conducted with equimolar amounts of reactants in organic solvents such as toluene, benzene, tetrahydrofuran, and under certain conditions, with organic bases such as triethylamine or pyridine. Reaction temperatures may range from 10° to 120° C.

The benzoylchlorides which serve as starting materials are prepared in known ways or are commercially available.

The 3-aminoisoxazoles to be employed as starting materials are prepared in several synthetic routes, which are outlined below.

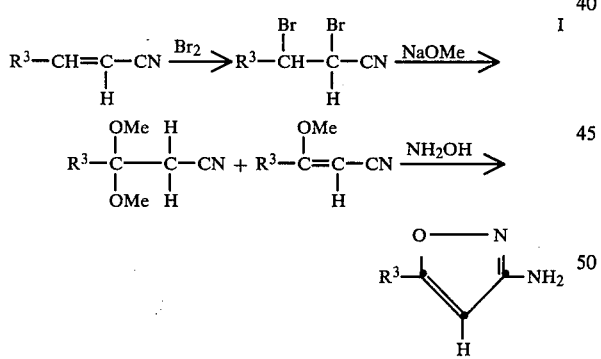

I

This synthetic route is illustrated by Examples 1–3 and 5–7 below.

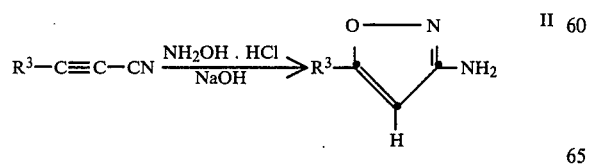

II

This synthetic route is illustrated by Example 9 below.

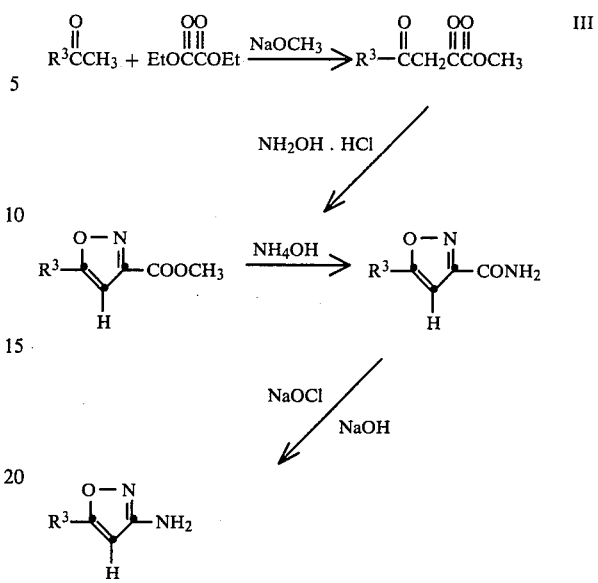

III

This synthetic route is illustrated by Examples 11–14 below.

IV The 2-substituted or 2,6-disubstituted-N-(2,6-dichlorobenzoyl)-N-(3-isoxazolyl)benzamide compounds of the present invention are prepared by reacting benzoylchloride with a 3-aminoisoxazole prepared according to synthetic routes I-III illustrated above. The reaction is as follows.

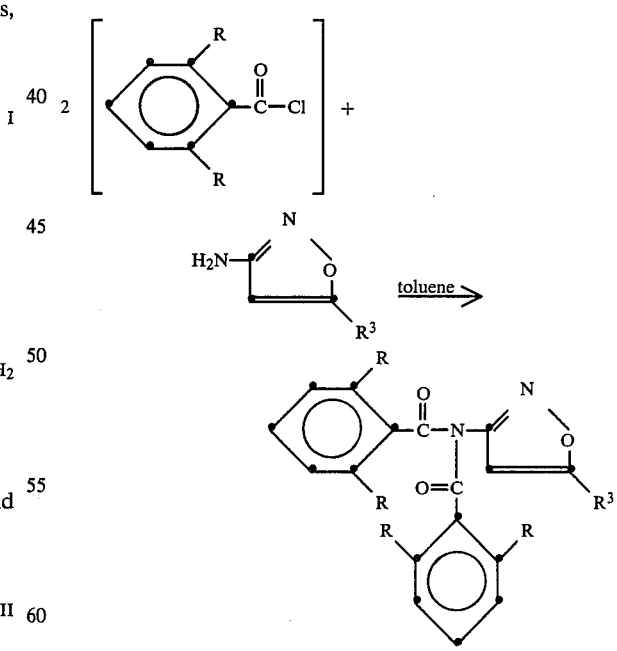

This synthesis route is illustrated by Example 16.

V The 2-substituted or 2,6-disubstituted-N-($C_1$-$C_3$ alkyl)-N-(3-isoxazolyl)benzamide compounds of the present invention are prepared as illustrated here with $CH_3$ for simplicity.

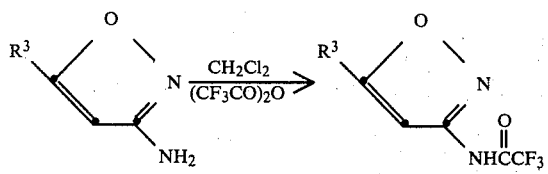

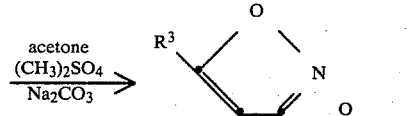

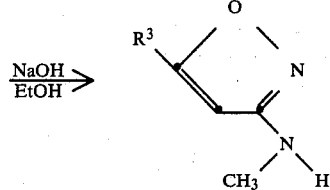

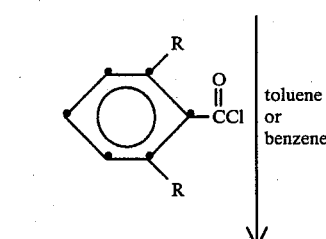

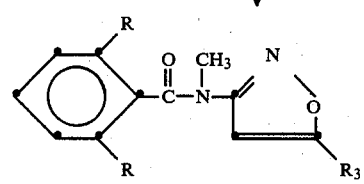

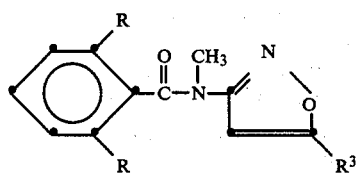

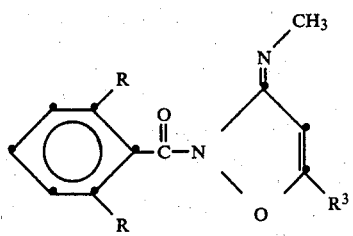

This synthetic route is illustrated by Examples 17–20.

In the above reactions, when each R in the benzoylchloride moiety is chloro, a mixture of endo- and exo-acylated isoxazole is obtained as follows:

plus

An alternative synthetic route for $R^1 = C_1-C_3$ alkyl compounds is as illustrated here with $CH_3$ for simplicity.

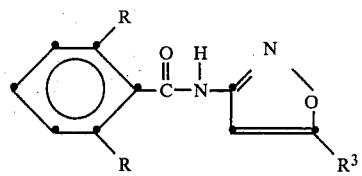

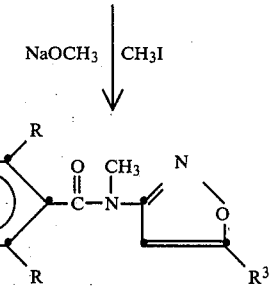

In the above procedure when each R in the benzoylchloride moiety is chloro, a mixture of endo- and exo-alkylated isoxazole is obtained as follows:

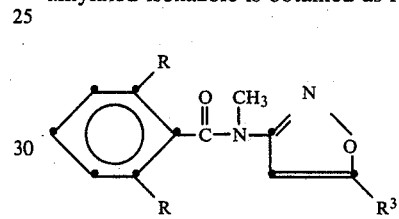

plus

This synthetic route is illustrated by Example 21.

The 5-aminoisoxazoles to be employed as starting materials are prepared as outlined below.

VI (Useful only for preparation of $R^4 = H$ compounds)

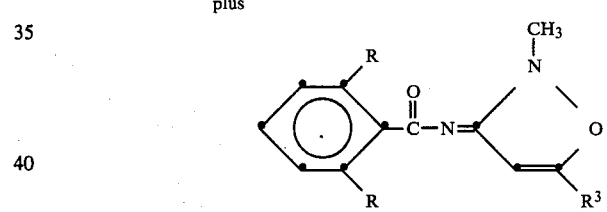

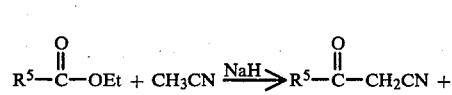

This synthesis route is illustrated by Examples 22–23 and 25–26 below.

VII (Useful only for preparation of $R^4$ = para-(trifluoromethyl)phenyl and $R^5 = H$ compounds)

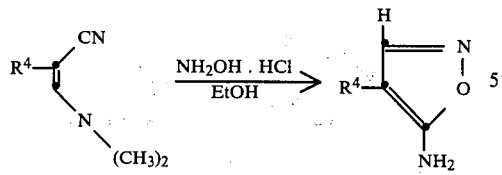

This synthesis route is illustrated by Examples 28–29.

The benzisoxazoles to be employed as starting materials are prepared according to known procedures as outlined below.

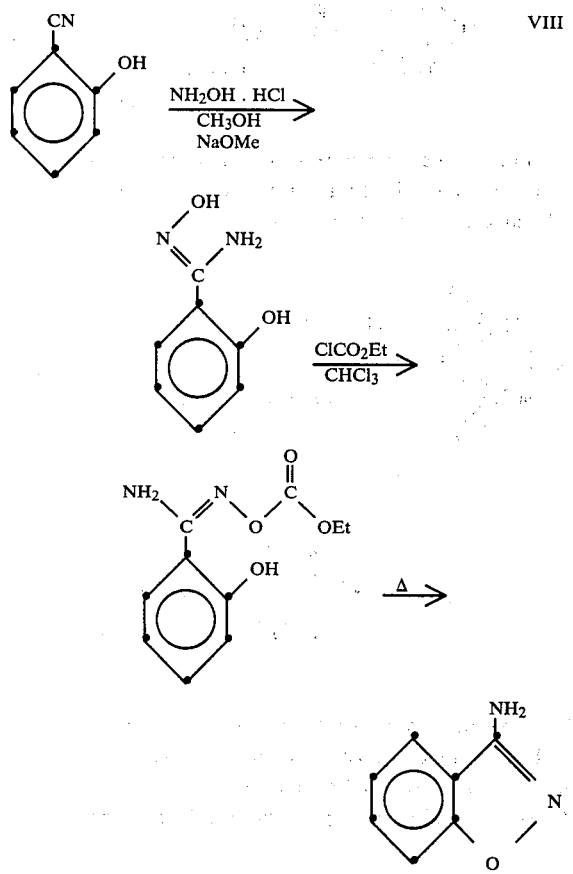

VIII

This synthesis route is illustrated by Examples 31–33.

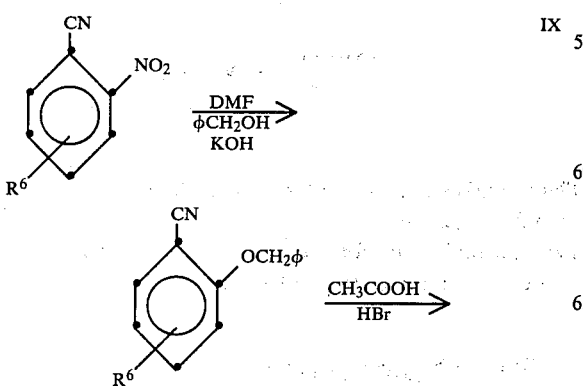

IX

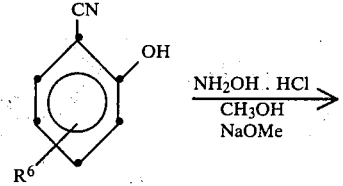

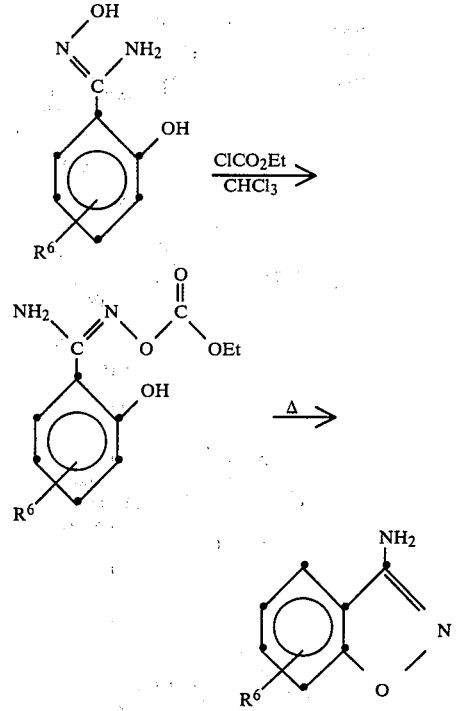

This synthesis route is illustrated by Examples 35–39.

EXAMPLE 1

3-(4-(TRIFLUOROMETHYL)PHENYL)-2,3-DIBROMOPROPIONITRILE 3-(4-(Trifluoromethyl)phenyl)acrylonitrile (1300 grams) was dissolved in chloroform, dried over $Na_2SO_4$, and filtered into a reaction flask. After bromine (1160 grams) was added in a steady stream and over ½ hour period, the reaction mixture was heated to reflux for 32 hours. Next the reaction mixture was stripped which resulted in a brown oil with some solids. The identity of the product was confirmed by NMR, yield 2098 grams.

EXAMPLE 2

MIXTURE OF 3-(4-(TRIFLUOROMETHYL)PHENYL)-3-METHOXYACRYLONITRILE PLUS 3-(4-(TRIFLUOROMETHYL)PHENYL)-3,3-DIMETHOXYPROPIONITRILE 3-(4-(Trifluoromethyl)phenyl)-2,3-dibromopropionitrile (2098 grams) was dissolved in methanol and chilled to 5° C. in an ice-bath. Next, over a 2 hour period, sodium methylate (95%) was added keeping the temperature between 5°–10° C. The reaction mixture was then allowed to warm to room temperature, was stirred for 33 hours, and was stripped to near dryness. Upon the addition of 8 l. ether the organic-inorganic mixture was slurried, slowly filtered, and the filtrate stripped again, resulting in a brown oil. NMR analysis confirmed that the oil was the desired mixture of products.

EXAMPLE 3

5-(4-(TRIFLUOROMETHYL)PHENYL)-3-AMINOISOXAZOLE 3-(4-Trifluoromethyl)phenyl)-3-methoxyacrylonitrile plus 3-(4-(trifluoromethyl)phenyl)-3,3-dimethoxypropionitrile (1330 grams as a mixture) and hydroxylamine.HCl (1180 grams) were dissolved in methanol and chilled to 20° C. in an ice-bath. Next sodium methylate (1890 grams) was added portionwise over a 1½ hour period keeping the temperature between 20°-30° C. The reaction mixture was then heated to reflux for about 17 hours and then cooled to 40° C. and filtered. After the filtrate was stripped and poured into ice-water with stirring, a light yellow solid precipitate formed which was filtered and identified by NMR analysis as the desired product, yield 994 grams.

EXAMPLE 4

2,6-DICHLORO-N-(5-(4-TRIFLUOROMETHYL)-PHENYL)-3-ISOXAZOLYL)BENZAMIDE 5-(4-(Trifluoromethyl)phenyl)-3-aminoisoxazole (1.5 grams) and 2,6-dichlorobenzoylchloride (2 grams in toluene) were heated at approximately 185° C. for 20 minutes. The reaction mixture was cooled to room temperature, ethanol was added, and then the resulting solid was filtered, washed with ether, and identified by NMR as 2,6-dichloro-N-(2,6-dichlorobenzoyl)-N-(5-(4-(trifluoromethyl)phenyl)-3-isoxazolyl)benzamide. The bis acylated solid (1.9 grams) was then refluxed for about 18 hours with 3 ml. 2 N NaOH and 100 ml. ethanol. After addition of HCl and the evaporation of the ethanol, the final product was filtered and then recrystallized from ethanol. The identity of the final product was confirmed by NMR analysis, m.p. 227°-229° C.

EXAMPLE 5

3-(4-BIPHENYLYL)-2,3-DIBROMOPROPIONITRILE 3-(4-Biphenylyl)acrylonitrile (10.5 grams) and bromine (9 grams) in 250 ml. of chloroform were refluxed overnight (about 18 hours). On cooling, the product precipitated and was separated by filtration, yield 16 grams. NMR confirmed the identity of the product.

EXAMPLE 6

MIXTURE OF 3-(4-BIPHENYLYL)-3-METHOXYACRYLONITRILE PLUS 3-(4-BIPHENYLYL)-3,3-DIMETHOXYPROPIONITRILE 3-(4-Biphenylyl)-2,3-dibromopropionitrile (16 grams) and sodium methoxide (4.7 grams) in 500 ml. of methanol were reacted in an ice bath. A solid precipitated at once and then the reaction mixture was stirred for 2 hours. The final product was determined by NMR to be a mixture of 3-(4-biphenylyl)-3-methoxyacrylonitrile plus 3-(4-biphenylyl)-3,3-dimethoxypropionitrile.

EXAMPLE 7

5-(4-BIPHENYLYL)-3-AMINOISOXAZOLE 3-(4-Biphenylyl)-3-methoxyacrylonitrile plus 3-(4-biphenylyl)-3,3-dimethoxypropionitrile (2.9 grams as a mixture from example 6), hydroxylamine hydrochloride (4.7 grams), and sodium methoxide (11.9 grams) were mixed in 500 ml. of methanol and refluxed for 48 hours. After the methanol was evaporated, water was added and the product, separated by filtration, yielded 1.2 grams. NMR confirmed the identity of the product.

EXAMPLE 8

2,6-DICHLORO-N-(5-(4-BIPHENYLYL)-3-ISOXAZOLYL)BENZAMIDE 5-(4-Biphenyl)-3-aminoisoxazole (500 mg.) and 2,6-dichlorobenzylchloride (1.3 grams) were heated together at 130° C. for twenty minutes. The reaction mixture was cooled to room temperature and then treated with ether/hexane. A precipitate formed which was filtered, dissolved in sodium hydroxide, and then precipitated in hydrochloric acid. After the final product was filtered and dried, the identity was confirmed by NMR analysis, m.p. 256°-259° C.

EXAMPLE 9

5-(3-(TRIFLUOROMETHYL)PHENYL)-3-AMINOISOXAZOLE

Hydroxylamine hydrochloride (1.6 grams), and sodium hydroxide (1.6 grams) were dissolved in 32 ml. of a 1:1 mixture of water and methanol at 0°-5° C. 3-(3-(Trifluoromethyl)phenyl)propiolonitrile (2.8 grams) in 10 ml. of methanol was added portionwise.

The reaction mixture was stirred overnight (about 18 hours) at 25° C. The solvent was evaporated; water was added to the residue and the product extracted with ether, washed with water, dried and evaporated to yield 1.4 grams. The identity of the desired product was confirmed by NMR.

EXAMPLE 10

2,6-DICHLORO-N-(5-(3-(TRIFLUOROMETHYL)-PHENYL-3-ISOXAZOLYL)BENZAMIDE 5-(3-(Trifluoromethyl)phenyl)-3-aminoisoxazole (0.8 grams) was dissolved in about 50 ml. of benzene to which 2,6-dichlorobenzoylchloride (1.047 grams) and triethylamine (0.5 grams) were added. The reaction mixture was placed under nitrogen and was constantly stirred while reacting at room temperature for about 60 hours. After the addition of 200 ml. of benzene, the reaction mixture was washed with dilute aqueous sodium bicarbonate and then dried over magnesium sulfate. Next the material recovered was dissolved in benzene and placed on a silica gel column using a benzene/ethyl-acetate eluant. Like fractions were combined using TLC and after the solvent was removed, the final product was recrystallized from benzene/pentane, m.p. 244°-246° C.

Calculated: C, 50.90; H, 2.26; N, 6.98; Found: C, 51.09; H, 2.40; N, 6.96.

EXAMPLE 11

4-CHLORO-α,γ-DIOXO-BENZENEBUTANOIC ACID(METHYL ESTER)

Sodium (6 grams) was placed in a 1 l. 3-necked flask with 200 ml. of ethanol. After cooling to −5° to 0° C., 4-chloroacetophenone (50 grams), ethyl oxylate (36.5 grams) and 50 ml. of ethanol were added. The reaction mixture was allowed to gradually warm to room temperature and was stirred approximately 18 hours overnight. The reaction mixture was then cooled and treated with approximately 125 ml. of 20% sulfuric acid. A solid precipitate formed which was filtered and washed with ethanol. The ethanol filtrate was reduced to about 200 ml. in volume, diluted with water and extracted with ether. The ether extract was washed with water, sodium bicarbonate, water, brine and then dried over MgSO$_4$. Filtration, followed by removal of the ether, afforded an oily solid which was a mixture of product and acetophenone. The oily solid was then thoroughly washed with ether and filtered. The filtrate was washed as described herein above, and, after the solvent was removed, a final product was recovered. The product was recrystallized from hexane, yield 39 grams, m.p. 56°–57° C.

Calculated: C, 48.19; H, 3.71; Found: C, 47.91; H, 3.65.

EXAMPLE 12

ETHYL-5-(4-CHLOROPHENYL)-3-ISOXAZOLECARBOXYLATE

4-Chloro-α,γ-dioxo-benzenebutanoic acid (methyl ester) (121 grams), hydroxylamine.HCl (35 grams), sodium bicarbonate (42 grams), and 600 ml. of ethanol were placed in a flask and heated to reflux for 2 hours. The reaction mixture was cooled to room temperature, treated with 2 l. of water, filtered, and dried overnight. An oily solid formed which was allowed to stand in ethanol for about 18 hours. After the solid was filtered off, water was added to the filtrate which, upon cooling and filtering, resulted in a pure white solid product. The identity of the desired product was confirmed by NMR, yield 48 grams.

EXAMPLE 13

5-(4-CHLOROPHENYL)-3-ISOXAZOLECARBOXAMIDE

Ethyl-5-(4-chlorophenyl)-3-isoxazolecarboxylate (139 grams) and 1.5 l. of conc. aqueous ammonium hydroxide were placed in a 2 l. 3-necked flask and stirred with a mechanical stirrer for 3 days. Following this, the reaction mixture was poured into 2 l. of water, filtered, and washed with water. The resulting dry solid was swirled with 1.6 l. of chloroform for ½ hour, filtered, and then dried in a vacuum oven for 3 hours, m.p. 224°–225° C.

Calculated: C, 53.95; H, 3.17; N, 12.58; Found: C, 54.00; H, 2.94; N, 12.45.

EXAMPLE 14

5-(4-CHLOROPHENYL)-3-AMINOISOXAZOLE 5-(4-(Chlorophenyl)-3-isoxazolylcarboxamide (58 grams), sodium hypochlorite (414 grams), and sodium hydroxide (23 grams) were reacted in a bomb at 150° C. for 10 minutes. The mixture was cooled to room temperature, extracted with chloroform, and then dried over sodium sulfate. After the removal of the solvent, the product residue was boiled with ethyl ether, cooled, and filtered, yield 28.6 grams, m.p. 141°–143° C.

Calculated: C, 55.34; H, 3.63; N, 14.39; Found: C, 55.52; H, 3.50; N, 14.46.

EXAMPLE 15

2,6-DICHLORO-N-(5-(4-CHLOROPHENYL)-3-ISOXAZOLYL)BENZAMIDE 5-(4-Chlorophenyl)-3-aminoisoxazole (25 grams) was placed in a 500 ml. 3-necked flask under an atmosphere of nitrogen. Following the addition of 150 ml. of toluene, the reaction mixture was stirred continuously and treated in rapid fashion (15 minutes), with 2,6-dichlorobenzoylchloride (60 grams). The mixture was then heated to reflux for 18 hours and allowed to gradually cool to room temperature. When the reaction mixture was further cooled to approximately 0° C. the final product precipitated. The product was filtered and recrystallized from acetone to yield 28 grams, m.p. 228°–229° C.

Calculated: C, 52.28; H, 2.47; N, 7.62; Found: C, 52.45; H, 2.43; N, 7.56.

EXAMPLE 16

2,6-DICHLORO-N-(2,6-DICHLOROBENZOYL)-N-(5-(4-CHLOROPHENYL)-3-ISOXAZOLYL)BENZAMIDE 5-(4-Chlorophenyl)-3-aminoisoxazole (400 milligrams prepared according to the teaching of Examples 11–14) was added to 2,6-dichlorobenzoylchloride (430 milligrams) in 50 ml. toluene and refluxed for 48 hours. The solvent was then evaporated and ethyl alcohol added; upon subsequent heating and filtering the bis acylated product was recovered; m.p. 219°–223° C.

Calculated: C, 51.10; H, 2.05; N, 5.18; Found: C, 51.25; H, 2.12; N, 5.36.

EXAMPLE 17

5-(4-CHLOROPHENYL)-3-N-(TRIFLUOROACETYL)AMINOISOXAZOLE 5-(4-Chlorophenyl)-3-aminoisoxazole (3.5 grams prepared according to the teaching of synthesis route III) and trifluoroacetic anhydride (4.2 grams) were stirred in 100 ml. methylene dichloride for approximately 1 hour. A solid formed which was filtered and then identified by NMR as the desired product, m.p.=249°–250° C.

Calculated: C, 45.46; H, 2.08; N, 9.64; Found: C, 45.43; H, 2.13; N, 9.83.

EXAMPLE 18

5-(4-CHLOROPHENYL)-3-N-METHYL-N-(TRIFLUOROACETYL)AMINOISOXAZOLE

Dimethyl sulfate (1.7 grams in 10 ml. acetone), 5-(4-chlorophenyl)-3-N-(trifluoroacetyl)aminoisoxazole (2.0 grams) and sodium carbonate (2.0 grams in 100 ml. acetate) were slowly mixed and stirred for about 20 hours. The solvent was evaporated and then methanol and water were added. Upon cooling, a solid formed which was filtered and then identified by NMR as the desired product, m.p.=130°–132° C.

EXAMPLE 19

5-(4-CHLOROPHENYL)-3-N-METHYLAMINOISOXAZOLE 5-(4-Chlorophenyl)-3-N-methyl-N-(trifluoroacetyl)aminoisoxazole (1.9 grams), and 20 ml. 2 N sodium hydroxide were heated in 30 ml. ethanol to near reflux until all the starting material dissolved. The desired product was filtered and collected upon cooling. The identity of the final product was confirmed by NMR, m.p.=171°–172° C.

Calculated: C, 57.57; H, 4.35; N, 13.43; Found: C, 57.34; H, 4.14; N, 13.52.

EXAMPLE 20

2,6-DIFLUORO-N-METHYL-N-(5-(4-CHLOROPHENYL)-3-ISOXAZOLYL)BENZAMIDE 5-(4-Chlorophenyl)-3-N-methylaminoisoxazole (600 mg.) and 2,6-difluorobenzoylchloride (600 mg.) were refluxed in 50 ml. toluene for about 18 hours. After the solvent was evaporated, ether was added and then the product was collected, washed with water, and recrystallized from ethanol. The identity of the final product was confirmed by NMR, m.p. 173°–175° C.

Calculated: C, 58.55; H, 3.18; N, 8.03; Found: C, 58.34; H, 2.95; N, 7.95.

Note that when 2,6-dichlorobenzoylchloride is used as the reactant, a mixture of exo- and endo-acylated isoxazole is obtained.

EXAMPLE 21

MIXTURE OF 2,6-DICHLORO-N-METHYL-N-(5-(4-CHLOROPHENYL)-3-ISOXAZOLYL)BENZAMIDE AND THE ENDO-ALKYLATED TAUTOMER THEREOF 2,6-Dichloro-N-(5-(4-chlorophenyl)-3-isoxazolyl)benzamide (1 gram prepared according to the teaching of synthesis route III and Example 15) and sodium methoxide (160 milligrams in 100 ml. methanol) were placed in a reaction vessel and stirred for about 15 minutes. Excess methyl iodide was added and the reaction mixture was then heated to reflux for 4 hours. Upon cooling a solid formed which was filtered and then recrystallized from ethanol. NMR analysis confirmed that the final product was a mixture of exo- and endo-alkylated isoxazole, m.p.=175°–178° C.

Calculated: C, 53.50; H, 2.91; N, 7.34; Found: C, 53.67; H, 2.98; N, 7.30.

EXAMPLE 22

3-(TRIFLUOROMETHYL)BENZOYLACETONITRILE

NaH (4.8 grams in a 50% oil dispersion) was placed in a 500 ml. 3-necked flask under an atmosphere of nitrogen and, after the addition of 80 ml. of THF, the mixture was heated to reflux. Next a solution of ethyl-3-(trifluoromethyl)benzoate (19 grams), acetonitrile, (5 grams) and THF (20 ml.) was added. Reflux was continued for 2 hours and then the reaction mixture was cooled and 250 ml. ether added. The organic layer was first extracted with 1 N NaOH, and then washed with brine and dried. Removal of the solvent afforded 11 grams of solid product, m.p. 58°–60° C.

EXAMPLE 23

3-(3-(TRIFLUOROMETHYL)PHENYL)-5-AMINOISOXAZOLE 3-(Trifluoromethyl)benzoylacetonitrile (3.8 grams) and 125 ml. ethanol were placed in a 500 ml. flask. The solution was treated with sodium acetate (12 grams) and hydroxylamine.hydrochloride (9 grams in 125 ml. water) and then heated to reflux for two hours. After cooling to room temperature, the ethanol was removed and the residue extracted with ether. The ether extracts were then washed with water, brine, and dried with MgSO4. The solid residue obtained was recrystallized from an ethanol/water solution, m.p. 89°–90° C.

EXAMPLE 24

2,6-DIFLUORO-N-(3-(3-(TRIFLUOROMETHYL)PHENYL)-5-ISOXAZOLYL)BENZAMIDE 3-(3-(Trifluoromethyl)phenyl)-5-aminoisoxazole (2.5 grams), triethylamine (1.5 grams) and 50 ml. benzene were placed in a 100 ml. flask. Next, 2,6-difluorobenzoylchloride (2.6 grams), dissolved in 5–10 ml. benzene, was added dropwise to the reaction mixture. The reaction was stirred at room temperature for 2 hours and was then warmed to 60° C. for about 18 hours. Following this, the mixture was washed with dilute sodium bicarbonate, water, brine, and then dried over MgSO4. The final product was first filtered, recrystallized from benzene/pentane, and then dried, m.p. 123°–126° C.

Calculated: C, 55.45; H, 2.46; N, 7.61; Found: C, 55.74; H, 2.35; N, 7.51.

EXAMPLE 25

4-CHLOROBENZOYLACETONITRILE

A 50% oil dispersion of NaH (24 grams) was placed in a 2 l. 3-necked flask and covered with 250 ml. THF. After heating to reflux, a solution composed of 55 ml. THF, ethyl-4-chlorobenzoate (57 grams), and acetonitrile (20.5 grams) was added in dropwise fashion. The reaction mixture started to solidify after the reactants were added so an additional 200 ml. of THF was added. The mixture was then heated to reflux for 2½ hours, cooled to room temperature, treated with 1 l. ether, and allowed to stand for 72 hours.

A solid product formed which was filtered, dissolved in water, acidified with conc. HCl and filtered. The identity of the final product was confirmed by NMR.

EXAMPLE 26

3-(4-CHLOROPHENYL)-5-AMINOISOXAZOLE

4-Chlorobenzoylacetonitrile (20 grams), sodium acetate (38 grams), hydroxylamine.HCl (29 grams), 350 ml. ethanol, and 350 ml. water were placed in a reaction vessel and heated to reflux for 3 hours. The final product can be collected either by removing the solvent and filtering directly or by extracting with chloroform, washing with 2 N NaOH, water, brine, and then drying with sodium sulfate. A yield of 5 grams of isoxazole was obtained and the structure was confirmed by NMR, m.p. 174°–175° C.

EXAMPLE 27

2,6-DICHLORO-N-(3-(4-CHLOROPHENYL)-5-ISOXAZOLYL)BENZAMIDE 3-(4-Chlorophenyl)-5-aminoisoxazole (1 gram) and 2,6-dichlorobenzoylchloride (5 grams) were placed in a 100 ml. reaction vessel and heated to near reflux for 1½ hours. The mixture was then cooled to room temperature and treated with 25 ml. of 2 N NaOH and 25 ml. ethanol. After refluxing for 2 hours, the ethanol was slowly removed at reduced pressure. A solid precipitate was collected by filtration. The remaining solution was treated with activated charcoal, filtered, and cooled to room temperature. The aqueous solution was extracted with chloroform. The chloroform was washed with water and dried (Na2SO4). Removal of the solvent afforded an oily product which was recrystallized from ether/hexane, m.p. 208°–209° C.

EXAMPLE 28

3-DIMETHYLAMINO-2-(4-(TRIFLUOROME-THYL)PHENYL)-ACRYLONITRILE 4-(Trifluoromethyl)phenylacetonitrile (6.0 g.) in 5 ml. dimethylformamide-dimethylacetal was refluxed for 2 hours. Water was added and the final product was filtered, dried, and identified by NMR analysis.

EXAMPLE 29

4-(4-(TRIFLUOROMETHYL)PHENYL)-5-AMINOISOXAZOLE

3-Dimethylamino-2-(4-(trifluoromethyl)phenyl)-acrylonitrile (2.5 g), and $NH_2OH\cdot HCl$ (1.5 g) were refluxed in ethanol for 2 hours. After evaporation of the solvent, water was added and the final product was filtered, recrystallized from methylene chloride, and identified by NMR analysis.

EXAMPLE 30

2,6-DIMETHOXY-N-(4-(4-(TRIFLUOROME-THYL)PHENYL)-5-ISOXAZOLYL)BENZAMIDE 4-(4-(Trifluoromethyl)phenyl)-5-aminoisoxazole (1.0 g) and 2,6-dimethoxybenzoylchloride (2 g) were refluxed in 100 ml. toluene for 3 hours. The reaction mixture was cooled and the final product was then collected and recrystallized from ethanol, m.p. 199°–201° C.

Calculated: C, 58.17; H, 3.85; N, 7.14; Found: C, 58.36; H, 3.61; N, 7.31.

EXAMPLE 31

2-HYDROXY-BENZAMIDE OXIME

2-Hydroxybenzonitrile (10 grams), hydroxylamine HCl (7 g.) in 150 ml. methanol, and sodium methoxide (9.0 grams) were refluxed for about 18 hours. The reaction mixture was then filtered and the ethanol evaporated. Next water was added and the product extracted into ethyl acetate. Drying and evaporation of the solvent left an oily product which solidified upon standing. The identity of the final product was confirmed by NMR and IR analysis.

EXAMPLE 32

2-HYDROXY-O-CARBOETHOXYBENZAMIDE OXIME

2-Hydroxy-benzamide oxime (2.4 grams) in 100 ml. chloroform was added dropwise to ethyl chloroformate (870 mg.) in 5 ml. chloroform. A precipitate formed and the reaction mixture was stirred for 17 hours, filtered, and the chloroform evaporated. The solid material was then dissolved in methanol and, after the addition of water, a precipitate formed which was identified by NMR and IR as the desired product, yield 1.4 grams.

EXAMPLE 33

3-AMINOBENZISOXAZOLE

2-Hydroxy-O-carboethoxybenzamide oxime (1.5 grams) was heated to 135°–140° C. under reduced pressure (5 mm.) and maintained at that temperature until the evolution of gas ceased (about 10 minutes). After cooling, ether was added and then the reaction mixture was filtered and chromatographed (ether-silica gel column chromatography). The material with the highest Rf value was a white solid which was identified by NMR and IR as the desired product, yield 500 mg.

EXAMPLE 34

2,6-DICHLORO-N-(3-BENZISOXAZOLYL)BENZAMIDE

3-Aminobenzisoxazole (2 gram), 2,6-dichlorobenzoylchloride (2 gram), and 50 ml. of toluene are heated at reflux for 16 hours. After evaporation of the solvent at reduced pressure, the resultant oily semi-solid is triturated with ether. The solid so formed is then washed with ether and water and constitutes the desired product.

EXAMPLE 35

2-(BENZYLOXY)-4-(TRIFLUOROMETHYL)BENZONITRILE

A solution of 2-nitro-4-(trifluoromethyl)-benzonitrile (21.5 grams in 350 ml. DMF at 0° C.) and benzyl alcohol (13 grams) was prepared and to this solution potassium hydroxide (10 grams) in 75 ml. water was added dropwise. The reaction mixture was then stirred for about 17 hours and poured into ice water. The resulting precipitate was filtered and identified by NMR as the desired product.

EXAMPLE 36

2-HYDROXY-4-(TRIFLUOROMETHYL)BENZONITRILE 2-(Benzyloxy)-4-(trifluoromethyl)benzonitrile (~20 grams) in 350 ml. acetic acid and 100 ml. 33% HBr was stirred overnight, refluxed for four hours, and then stirred overnight again. Next the reaction mixture was stripped to a small volume and poured into ice water. The crude precipitate which formed was stirred in hexane, filtered, and was identified by NMR as the desired product, yield 9.3 grams.

EXAMPLE 37

2-HYDROXY-4-(TRIFLUOROMETHYL)BENZAMIDE OXIME

The desired compound was prepared according to the teaching of Example 31. The identity of the desired product was confirmed by NMR, yield 6.1 grams from 9.3 grams of starting material.

EXAMPLE 38

2-HYDROXY-4-(TRIFLUOROMETHYL)-O-CARBOETHOXYBENZAMIDE OXIME

The desired compound was prepared according to the teaching of Example 32. The identity of the desired product was confirmed by NMR.

Calculated: C, 45.21; H, 3.79; N, 9.59; Found: C, 44.96; H, 3.76; N, 9.42.

EXAMPLE 39

7-(TRIFLUOROMETHYL)-3-AMINOBENZISOXAZOLE

2-Hydroxy-4-(trifluoromethyl)-O-carboethoxybenzamide oxime (2.1 grams) was heated in a 50 ml. flask under vacuum to a temperature of 190°–195° C. The temperature was maintained at 185°–190° C. until the evolution of gas ceased (about 10 minutes) and then, after cooling, the reaction material was dissolved in ethyl acetate and filtered. TLC (ether) showed no starting material and NMR confirmed the identity of the product.

EXAMPLE 40

2,6-DICHLORO-N-(7-(TRIFLUOROMETHYL)-3-BENZISOXAZOLYL)BENZAMIDE 7-(Trifluoromethyl)-3-aminobenzisoxazole (2 gram), 2,6-dichlorobenzoylchloride (2 gram), and 50 ml. of toluene are heated at reflux for 16 hours. After evaporation of the solvent at reduced pressure, the resultant oily semi-solid is triturated with ether. The solid so formed is then washed with ether and water and constitutes the desired product.

Other representative compounds of the present invention, synthesized in accordance with the foregoing teaching, include the following.

| Example No. | Compound Name | Melting Point |
|---|---|---|
| 41 | 2,6-Dichloro-N-(3-(3-chlorophenyl)-5-isoxazolyl)benzamide | 215–218° C. |
| 42 | 2,6-Dichloro-N-(5-phenyl-3-isoxazolyl)benzamide | 209–211° C. |
| 43 | 2,6-Dichloro-N-(5-(4-fluorophenyl)-3-isoxazolyl)benzamide | 220–222° C. |
| 44 | 2,6-Dichloro-N-(5-(3-chlorophenyl)-3-isoxazolyl)benzamide | 227–229° C. |
| 45 | 2,6-Dichloro-N-(5-(4-tolyl)-3-isoxazolyl)benzamide | 243–245° C. |
| 46 | 2,6-Dichloro-N-(5-(3,4-dichlorophenyl)-3-isoxazolyl)benzamide | 275–277° C. |
| 47 | 2,6-Dichloro-N-(5-(4-bromophenyl)-3-isoxazolyl)benzamide | 268–270° C. |
| 48 | 2,6-Dichloro-N-(5-(3-fluorophenyl)-3-isoxazolyl)benzamide | 208–210° C. |
| 49 | 2-Chloro-6-methyl-N-(5-(3-chlorophenyl)-3-isoxazolyl)benzamide | 228–229° C. |
| 50 | 2-Chloro-N-(5-(3-(trifluoromethyl)phenyl)-3-isoxazolyl)benzamide | 187–189° C. |
| 51 | 2,6-Dichloro-N-(5-(3-(phenoxy)phenyl)-3-isoxazolyl)benzamide | 157–160° C. |
| 52 | 2,6-Difluoro-N-(3-(3-tolyl)-5-isoxazolyl)benzamide | 128–129° C. |
| 53 | 2,6-Dimethoxy-N-(3-(3-tolyl)-5-isoxazolyl)benzamide | 165–167° C. |
| 54 | 2,6-Dimethoxy-N-(3-(2-tolyl)-5-isoxazolyl)benzamide | 199–202° C. |
| 55 | 2,6-Dimethyl-N-(3-(2-tolyl)-5-isoxazolyl)benzamide | 164–166° C. |
| 56 | 2,6-Difluoro-N-(5-(4-chlorophenyl)-3-isoxazolyl)benzamide | 275–276° C. |
| 57 | 2,6-Difluoro-N-(3-(3-chlorophenyl)-5-isoxazolyl)benzamide | 188–190° C. |

The compounds of the present invention are useful for the control of insects of various orders, including Coleoptera such as Mexican bean beetle, Colorado potato beetle, white grubs; Diptera, such as yellow-fever mosquitoes, house fly; Lepidoptera, such as European corn borer, bollworm, tobacco budworm, *Spodoptera littoralis,* southern armyworm, fall armyworm, sod webworm, tobacco hornworm, loopers, beet armyworm, diamond back moth, imported cabbage worm; Orthoptera, such as German cockroach, American cockroach; and Thysanoptera, such as thrips.

The compounds of the present invention are additionally useful for the control of other insects such as horn fly, common cattle grub, stable fly, face fly, mosquitoes, screwworm, tabanid fly, army cutworm, midges, southwestern corn borer, lesser cornstalk borer, horse bot fly, cabbage maggot, velvet bean caterpillar, pecan nut casebearer, pink bollworm, hickory shuckworm, walnut caterpillar, green cloverworm, alfalfa caterpillar, leaf miner fly, yellowstriped armyworm, rednecked peanutworm, stalk borer, sunflower moth, tomato pin worm, Oriental fruit moth, plum curculio, peachtree borer, melon fly, lesser peachtree borer, grape root borer, black fly, nose bot fly, grape berry moth, sheep ked, leaf rollers, and spruce bud worms.

It is believed that the present compounds act by interfering with the mechanism of metamorphosis which occurs in insects, causing the death of the insects. It is also believed that ingestion by the insects is necessary to invoke this mechanism. While the death of any given insect may be delayed until that insect reaches some stage of metamorphosis, the net result of this activity is the control and suppression of insects.

Therefore, in another embodiment, the present invention is directed to a method of suppressing insects which comprises applying to a locus of the insects an effective amount of a compound of the present invention. The locus can be any environment inhabited by insects to be controlled, such as soil, air, water, foods, vegetation, manure, inert objects, stored matter such as grain, and the like. The compounds of the invention will normally be applied by spraying, to the locus in an amount varying from 0.001 to 10 lbs/acre depending on the nature of the locus, the type and severity of the insect infestation, etc. Preferably the compounds are applied in an amount varying from 0.1 to 1 lb/acre.

Preferably the compounds of the present invention are supplied in a formulation, for ease of application. The compounds can be formulated with various adjuvants, including water, organic liquids, surface-active agents, inert solids, and the like. Suitable surface-active agents include anionic agents, such as sodium lauryl sulfate, sodium dodecylbenzenesulfonate, and the like; and nonionic agents, such as polyoxyethylene glycol nonylphenyl ether. Mixtures are often desirably employed. The formulation can take the form of a liquid, dust, granule, aerosol, and so forth containing from 0.1 to 80% of a compound of the invention. Specifically the formulation may be an emulsifiable concentrate having 12–50% actives, a wettable powder having up to 80% actives, a granule having up to 10% actives, and a dust having up to 1% actives. In addition to the amounts of actives specified, the balance of the ingredients for the previously listed formulations is comprised of the various adjuvants listed above. These adjuvants and their use in formulations such as those exemplified herein, are well known and appreciated in the art. Moreover it is understood that those with ordinary skill will readily select one or more of the above adjuvants for use in formulating the present compounds in accordance with the percentages disclosed for the specific formulations. The formulations also can be designed to slowly release the active compound or to make the active compound immediately available. Many methods of formulation are known in the art and can be employed to implement the present invention.

The concentration of active agent in the formulation is not critical, inasmuch as an effective concentration will vary with the nature of the locus to be treated, the severity of insect infestation, the susceptibility of the particular insects involved, etc. In general, concentrations ranging from about 0.1 to 1000 ppm give good results. As exemplified by Table 2, below, lesser concentrations of from about 5 to about 100 ppm have given good control of southern armyworm larvae.

The compounds of the present invention also have non-insecticidal application and utility. For example, the compounds are useful as terrestrial herbicides and as such are effective and valuable for the elimination of unwanted weeds which are agriculturally troublesome and aesthetically disagreeable.

While all the compounds of the present invention show considerable efficacy in the control and eradication of undesirable insect pests, certain compounds are more effective than others. Accordingly, preferred compounds of the present invention are those wherein each R, as defined herein, is chloro; $R^1$, as defined herein, is H; and $R^2$, as defined herein, is 3-isoxazolyl with a 4-bromo-, 4-chloro-, or 4-fluorophenyl substituent at the 5-position. One of the most useful compounds of this preferred group has been shown to be 2,6-dichloro-N-(5-(4-fluorophenyl)-3-isoxazolyl)-benzamide. While it is understood that there are many other useful and potentially important embodiments of the present invention, the preferred embodiment is as disclosed herein above.

The insecticidal activity of the present compounds was determined by testing the efficacy of formulations of the compounds against Mexican bean beetle larvae (*Epilachna varivestis*), and against southern armyworm larvae (*Spodoptera eridania*). These insects are members of the Coleoptera and Lepidoptera orders of insects, respectively. The formulations were applied to the foliage of plants and the larvae were subsequently permitted to feed on the foliage. The compounds were tested in a plurality of concentrations, from a concentration of about 1000 ppm. to about 1 ppm.

Each compound to be tested was formulated by dissolving the compound in a solvent made up with small amounts of Toximul R and Toximul S, typically 5.9 grams and 4.0 grams, respectively, per liter of 1:1 anhydrous ethanol and acetone. Water was then added to obtain a solution containing the compound in a concentration of 1000 parts per million. A portion was diluted further with water containing small amounts of Toximul R and Toximul S, to obtain treating solutions of lesser concentrations. It is understood that those skilled in the art will vary the amounts of water and Toximul R and Toximul S depending on the particular concentration of active compound desired. Each of Toximul R and Toximul S is a sulfonate/nonionic blend produced by Stepan Chemical Company, Northfield, Illinois.

Each solution of test compound was sprayed onto two 4-inch square pots of bean plants containing 6 to 10 plants per pot. The plants were allowed to dry and then 12 leaves were removed and the cut ends wrapped in water-soaked cellucotton. The leaves were divided between six 100×20 mm. plastic petri dishes. Five second-instar Mexican bean beetle larvae (*Epilachna varivestis*) and five second- and third-instar southern armyworm larvae (*Spodoptera eridania*) were placed in each of three dishes. The dishes were then placed in a room wherein the temperature and relative humidity were controlled at about 78° F. and about 51 percent, respectively, for a period of four days, at which time the first evaluation of the effects of the test compounds was made. After this evaluation, two fresh leaves from the original treated pots were placed in each dish. The dishes were again maintained in the temperature and humidity controlled room for an additional three days until the final seven-day evaluation was made.

Insecticidal effect was determined by counting the number of living larvae per dish. All the treatments were compared to solvent controls and nontreated controls. The rating code (percent of control) used was as follows:

0=0%
1=1–50%
2=51–99%
3=100% control

The results of this test are set forth in Table 1, which follows. In the table column 1 identifies the compounds by the number of the preparative example; column 2 lists the concentration of the test compound in the formulation; and columns 3 through 6 give the Rating Code at days 4 and 7 for the two insects against which the compounds were tested. An N/T entry means 'not tested'.

TABLE 1

| Example No. | Appln. Rate ppm | Insect Control | | | |
|---|---|---|---|---|---|
| | | Mexican Bean Beetle | | Southern Armyworm | |
| | | 4 days | 7 days | 4 days | 7 days |
| 4 | 1000 | 0 | 0 | 3 | 3 |
| | 100 | 0 | 0 | 3 | 3 |
| 8 | 1000 | 0 | 0 | 1 | 3 |
| | 100 | 0 | 0 | 0 | 2 |
| 10 | 1000 | 0 | 2 | 3 | 3 |
| | 100 | 0 | 2 | 3 | 3 |
| 15 | 1000 | 0 | 1 | 3 | 3 |
| | 100 | 0 | 1 | 3 | 3 |
| 16 | 1000 | 0 | 1 | 2 | 3 |
| | 100 | 0 | 1 | 0 | 2 |
| 21 | 1000 | 2 | 2 | 3 | 3 |
| | 100 | 0 | 0 | 3 | 3 |
| 24 | 1000 | 2 | 3 | 0 | 1 |
| | 100 | 1 | 1 | N/T | N/T |
| 27 | 1000 | 0 | 1 | 3 | 3 |
| | 100 | 0 | 0 | 1 | 1 |
| 30 | 1000 | 0 | 0 | 0 | 2 |
| | 100 | 0 | 0 | 0 | 1 |
| 41 | 1000 | 0 | 1 | 3 | 3 |
| | 100 | 0 | 0 | 1 | 2 |
| 42 | 1000 | 2 | 3 | 1 | 2 |
| | 100 | 2 | 2 | 1 | 2 |
| 43 | 1000 | 0 | 2 | 2 | 3 |
| | 100 | 0 | 2 | 3 | 3 |
| 44 | 1000 | 0 | 2 | 3 | 3 |
| | 100 | 0 | 0 | 2 | 2 |
| 45 | 1000 | 1 | 1 | 2 | 3 |
| | 100 | 0 | 0 | 0 | 0 |
| 46 | 1000 | 0 | 0 | 2 | 3 |
| | 100 | 0 | 0 | 1 | 3 |
| 47 | 1000 | 0 | 0 | 3 | 3 |
| | 100 | 0 | 0 | 2 | 3 |
| 48 | 1000 | 0 | 2 | 2 | 2 |
| | 100 | 0 | 0 | 0 | 1 |
| 49 | 1000 | 0 | 0 | 2 | 3 |
| | 100 | 0 | 0 | 0 | 1 |
| 50 | 1000 | 1 | 2 | 0 | 1 |
| | 100 | 1 | 2 | 0 | 0 |
| 51 | 1000 | 2 | 3 | 2 | 3 |
| | 100 | 1 | 2 | 0 | 2 |
| 52 | 1000 | 0 | 2 | 0 | 0 |
| | 100 | 2 | 2 | N/T | N/T |
| 53 | 1000 | 1 | 2 | 3 | 3 |
| | 100 | 1 | 1 | 3 | 3 |
| 54 | 1000 | 1 | 3 | 0 | 0 |
| | 100 | 1 | 2 | N/T | N/T |
| 55 | 1000 | 1 | 3 | 0 | 0 |
| | 100 | 0 | 0 | 0 | 0 |
| 56 | 1000 | N/T | N/T | 3 | 3 |
| | 100 | N/T | N/T | 3 | 3 |
| 57 | 1000 | N/T | N/T | 1 | 3 |
| | 100 | N/T | N/T | 0 | 0 |

The compounds of the present invention were also tested in the same procedure described above but at lower concentrations. In these tests, percent control was determined by counting the number of living larvae per dish and using Abbott's formula [W. W. Abbott, "A Method of Computing the Effectiveness of an Insecticide", *J. Econ. Entomol.* 18, 265-267 (1925)]:

Percent Control =
$$\frac{\text{No. of survivors in control} - \text{No. of survivors in treatment} \times 100}{\text{No. survivors in control}}$$

The results are set forth in Table 2, which follows.

TABLE 2

| Example No. | Appln. Rate ppm. | Insect Control (%) | | | |
|---|---|---|---|---|---|
| | | Mexican Bean Beetle | | Southern Armyworm | |
| | | 4 days | 7 days | 4 days | 7 days |
| 4 | 10 | N/T | N/T | 13 | 36 |
| | 25 | N/T | N/T | 53 | 93 |
| | 50 | N/T | N/T | 53 | 100 |
| | 100 | N/T | N/T | 100 | 100 |
| 8 | 10 | N/T | N/T | 13 | 86 |
| | 25 | N/T | N/T | 33 | 100 |
| | 50 | N/T | N/T | 40 | 100 |
| | 100 | N/T | N/T | 53 | 100 |
| 10 | 10 | N/T | N/T | 60 | 100 |
| | 25 | N/T | N/T | 100 | 100 |
| | 50 | N/T | N/T | 100 | 100 |
| | 100 | N/T | N/T | 100 | 100 |
| | 1.0 | N/T | N/T | 0 | 0 |
| | 2.5 | N/T | N/T | 7 | 7 |
| | 5. | N/T | N/T | 27 | 86 |
| | 10 | N/T | N/T | 93 | 100 |
| 15 | 10 | N/T | N/T | 87 | 100 |
| | 25 | N/T | N/T | 100 | 100 |
| | 50 | N/T | N/T | 100 | 100 |
| | 100 | N/T | N/T | 100 | 100 |
| | 1.0 | N/T | N/T | 7 | 39 |
| | 2.5 | N/T | N/T | 36 | 100 |
| | 5 | N/T | N/T | 86 | 100 |
| | 10 | N/T | N/T | 100 | 100 |
| 21 | 10 | N/T | N/T | 27 | 100 |
| | 25 | N/T | N/T | 40 | 100 |
| | 50 | N/T | N/T | 100 | 100 |
| | 100 | N/T | N/T | 100 | 100 |
| 41 | 10 | N/T | N/T | 0 | 0 |
| | 25 | N/T | N/T | 0 | 13 |
| | 50 | N/T | N/T | 7 | 80 |
| | 100 | N/T | N/T | 10 | 100 |
| 42 | 10 | N/T | N/T | 0 | 0 |
| | 25 | N/T | N/T | 0 | 7 |
| | 50 | N/T | N/T | 0 | 13 |
| | 100 | N/T | N/T | 20 | 68 |
| 43 | 10 | N/T | N/T | 100 | 100 |
| | 25 | N/T | N/T | 100 | 100 |
| | 50 | N/T | N/T | 100 | 100 |
| | 100 | N/T | N/T | 100 | 100 |
| | 1.0 | N/T | N/T | 20 | 27 |
| | 2.5 | N/T | N/T | 86 | 100 |
| | 5 | N/T | N/T | 100 | 100 |
| | 10 | N/T | N/T | 100 | 100 |
| 44 | 10 | N/T | N/T | 0 | 7 |
| | 25 | N/T | N/T | 0 | 14 |
| | 50 | N/T | N/T | 60 | 70 |
| | 100 | N/T | N/T | 100 | 100 |
| 46 | 10 | N/T | N/T | 20 | 93 |
| | 25 | N/T | N/T | 93 | 100 |
| | 50 | N/T | N/T | 100 | 100 |
| | 100 | N/T | N/T | 100 | 100 |
| | 1.0 | N/T | N/T | 0 | 0 |
| | 2.5 | N/T | N/T | 0 | 0 |
| | 5 | N/T | N/T | 0 | 60 |
| | 10 | N/T | N/T | 27 | 93 |
| 47 | 10 | N/T | N/T | 11 | 100 |
| | 25 | N/T | N/T | 80 | 100 |
| | 50 | N/T | N/T | 100 | 100 |
| | 100 | N/T | N/T | 100 | 100 |
| | 1.0 | N/T | N/T | 0 | 13 |
| | 2.5 | N/T | N/T | 13 | 93 |
| | 5 | N/T | N/T | 80 | 100 |
| | 10 | N/T | N/T | 93 | 100 |

TABLE 2-continued

| Example No. | Appln. Rate ppm. | Insect Control (%) | | | |
|---|---|---|---|---|---|
| | | Mexican Bean Beetle | | Southern Armyworm | |
| | | 4 days | 7 days | 4 days | 7 days |
| 56 | 1.0 | N/T | N/T | 0 | 0 |
| | 2.5 | N/T | N/T | 53 | 72 |
| | 5 | N/T | N/T | 53 | 87 |
| | 10 | N/T | N/T | 80 | 100 |

I claim:
1. Compounds of the formula

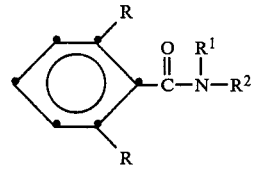

wherein each R is selected from the group consisting of
H,
F,
Br,
Cl,
CH$_3$, or
OCH$_3$,
with the proviso that each R cannot simultaneously represent H;
R$^1$=H, C$_1$-C$_3$ alkyl, or 2,6-dichlorobenzoyl, subject to the proviso that when R$^1$=dichlorobenzoyl, both R groups simultaneously represent chloro;
R$^2$=a 3-isoxazolyl of the formula

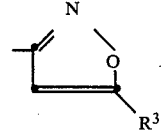

with the proviso that each R cannot simultaneously represent methyl or methoxy and subject to the further proviso that when one R represents methyl the other R cannot simultaneously represent methoxy, wherein
R$^3$=unsubstituted phenyl, 3,4-dihalophenyl, or a meta- or para-substituted phenyl of which the substituent is Br, Cl, F, I, C$_1$-C$_3$ alkyl, O$_m$C$_n$F$_{2n+1}$, O$_m$C$_n$F$_{2n}$H, $\phi$, or -O$\phi$, m=0-1 and n independently=1-2 with the proviso that when R$^1$ represents 2,6-dichlorobenzoyl, R$^3$ cannot represent unsubstituted phenyl, or meta- or para-(trifluoromethyl)-phenyl; or
R$^2$=a 5-isoxazolyl of the formula

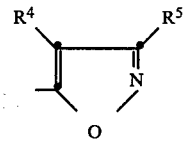

with the proviso that R$^1$=H, and subject to the further proviso that when one R represents CH$_3$ or OCH$_3$ the other R cannot simultaneously represent halo, wherein $R^4$=H, or para-(trifluoromethyl)phenyl;

$R^5$=H, para-chlorophenyl, or an ortho- or meta-substituted phenyl of which the substitutent is Cl, $CH_3$, or $CF_3$ with the proviso that
(a) when $R^5$ is para-chlorophenyl, neither R can represent H,
(b) when $R^5$ is meta-(trifluoromethyl)-phenyl, each R cannot simultaneously represent an $OCH_3$ moiety,
(c) $R^4$ and $R^5$ cannot simultaneously represent H,
(d) when $R^4$ represents para-(trifluoromethyl)phenyl, $R^5$ represents H; or $R^2$=a 3-benzisoxazolyl of the formula

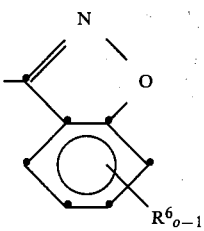

subject to the proviso that $R^1$=H, and subject to the further proviso that each R cannot simultaneously represent methyl or methoxy and when one R represents methyl the other R cannot simultaneously represent methoxy, wherein $R^6$=halo, $C_1$-$C_3$ alkyl, $O_mC_nF_{2n+1}$, or $O_mC_nF_{2n}H$, m=0-1 and n independently=1-2;

or in the case of $R^1$=$C_1$-$C_3$ alkyl and each R simultaneously=chloro, the endo-alkylated and endo-acylated isoxazole tautomers thereof.

2. The compound of claim 1 wherein $R^2$ is a 3-isoxazolyl as recited in claim 1.

3. The compound of claim 2 wherein $R^3$ is selected from the group consisting of
3-bromophenyl,
4-bromophenyl,
3-chlorophenyl,
4-chlorophenyl,
3-fluorophenyl,
4-fluorophenyl, or
3,4-dichlorophenyl.

4. The compound of claim 3 which is 2,6-dichloro-N-(5-(3-bromophenyl)-3-isoxazolyl)benzamide.

5. The compound of claim 3 which is 2,6-difluoro-N-(5-(3-bromophenyl)-3-isoxazolyl)benzamide.

6. The compound of claim 3 which is 2,6-dibromo-N-(5-(3-bromophenyl-3-isoxazolyl)benzamide.

7. The compound of claim 3 which is 2,6-dichloro-N-(5-(4-bromophenyl)-3-isoxazolyl)benzamide.

8. The compound of claim 3 which is 2,6-dichloro-N-(5-(3-chlorophenyl)-3-isoxazolyl)benzamide.

9. The compound of claim 3 which is 2,6-dichloro-N-(5-(4-chlorophenyl)-3-isoxazolyl)benzamide.

10. The compound of claim 3 which is 2-chloro-N-(5-(4-chlorophenyl)-3-isoxazolyl)benzamide.

11. The compound of claim 3 which is 2,6-difluoro-N-(5-(4-chlorophenyl)-3-isoxazolyl)benzamide.

12. The compound of claim 3 which is 2,6-dibromo-N-(5-(4-chlorophenyl)-3-isoxazolyl)benzamide.

13. The compound of claim 3 which is 2-chloro-6-methyl-N-(5-(3-chlorophenyl)-3-isoxazolyl)benzamide.

14. The compound of claim 3 which is 2,6-dichloro-N-(5-(3-fluorophenyl)-3-isoxazolyl)benzamide.

15. The compound of claim 3 which is 2,6-dichloro-N-(5-(4-fluorophenyl)-3-isoxazolyl)benzamide.

16. The compound of claim 3 which is 2,6-difluoro-N-(5-(4-fluorophenyl)-3-isoxazolyl)benzamide.

17. The compound of claim 3 which is 2,6-dibromo-N-(5-(4-fluorophenyl)-3-isoxazolyl)benzamide.

18. The compound of claim 3 which is 2,6-dichloro-N-(5-(3,4-dichlorophenyl)-3-isoxazolyl)benzamide.

19. The compound of claim 1 wherein $R^1$ is methyl as recited in claim 1.

20. The compound of claim 19 which is 2,6-difluoro-N-methyl-N-(5-(4-chlorophenyl)-3-isoxazolyl)benzamide.

21. The compound of claim 19 which is a mixture of 2,6-dichloro-N-methyl-(5-(4-chlorophenyl)-3-isoxazolyl)benzamide and the endo-alkylated or endoacylated isoxazole tautomers thereof.

22. The compound of claim 1 wherein $R^1$ is 2,6-dichlorobenzoyl as recited in claim 1.

23. The compound of claim 22 which is 2,6-dichloro-N-2,6-dichlorobenzoyl-N-(5-(4-chlorophenyl)-3-isoxazolyl)benzamide.

24. The compound of claim 2 wherein $R^3$ is selected from the group consisting of
4-tolyl,
3-(trifluoromethyl)phenyl,
4-(trifluoromethyl)phenyl,
3-phenoxy,
4-biphenylyl, or phenyl.

25. The compound of claim 24 which is 2,6-dichloro-N-(5-(4-tolyl)3-isoxazolyl)benzamide.

26. The compound of claim 24 which is 2,6-dichloro-N-(5-(3-(trifluoromethyl)phenyl)-3-isoxazolyl)benzamide.

27. The compound of claim 24 which is 2-chloro-N-(5-(3-(trifluoromethyl)phenyl)-3-isoxazolyl)benzamide.

28. The compound of claim 24 which is 2,6-difluoro-N-(5-(3-(trifluoromethyl)phenyl)-3-isoxazolyl)benzamide.

29. The compound of claim 24 which is 2,6-dibromo-N-(5-(3-(trifluoromethyl)phenyl)-3-isoxazolyl)benzamide.

30. The compound of claim 24 which is 2,6-dichloro-N-(5-(4-(trifluoromethyl)phenyl)-3-isoxazolyl)benzamide.

31. The compound of claim 24 which is 2,6-difluoro-N-(5-(4-trifluoromethyl)phenyl)-3-isoxazolyl)benzamide.

32. The compound of claim 24 which is 2,6-dibromo-N-(5-(4-(trifluoromethyl)phenyl)-3-isoxazolyl)benzamide.

33. The compound of claim 24 which is 2,6-dichloro-N-(5-(3-(phenoxy)phenyl)-3-isoxazolyl)benzamide.

34. The compound of claim 24 which is 2,6-dichloro-N-(5-(4-biphenylyl)-3-isoxazolyl)benzamide.

35. The compound of claim 24 which is 2,6-difluoro-N-(5-(4-biphenylyl)-3-isoxazolyl)benzamide.

36. The compound of claim 24 which is 2,6-dibromo-N-(5-(4-biphenylyl)-3-isoxazolyl)benzamide.

37. The compound of claim 24 which is 2,6-dichloro-N-(5-phenyl-3-isoxazolyl)benzamide.

38. The compound of claim 1 wherein $R^2$ is a 5-isoxazolyl as recited in claim 1.

39. The compound of claim 38 wherein $R^5$ is selected from the group consisting of
hydrogen,
3-chlorophenyl,
4-chlorophenyl, 2-tolyl,
3-tolyl, or 3-(trifluoromethyl)phenyl.

40. The compound of claim 39 which is 2,6-dimethoxy-N-(4-(4-(trifluoromethyl)phenyl)-5-isoxazolyl)-benzamide.

41. The compound of claim 39 which is 2,6-dichloro-N-(3-(3-chlorophenyl)-5-isoxazolyl)benzamide.

42. The compound of claim 39 which is 2,6-difluoro-N-(3-(3-chlorophenyl)-5-isoxazolyl)benzamide.

43. The compound of claim 39 which is 2,6-dichloro-N-(3-(4-chlorophenyl)-5-isoxazolyl)benzamide.

44. The compound of claim 39 which is 2,6-dimethyl-N-(3-(2-tolyl)-5-isoxazolyl)benzamide.

45. The compound of claim 39 which is 2,6-dimethoxy-N-(3-(2-tolyl)-5-isoxazolyl)benzamide.

46. The compound of claim 39 which is 2,6-dimethoxy-N-(3-(3-tolyl)-5-isoxazolyl)benzamide.

47. The compound of claim 39 which is 2,6-difluoro-N-(3-(3-tolyl)-5-isoxazolyl)benzamide.

48. The compound of claim 39 which is 2,6-difluoro-N-(3-(3-(trifluoromethyl)phenyl)-5-isoxazolyl)-benzamide.

49. The compound of claim 1 wherein $R^2$ is a 3-benzisoxazolyl as recited in claim 1.

50. The compound of claim 49 which is 2,6-dichloro-N-(3-benzisoxazolyl)benzamide.

51. The compound of claim 49 wherein $R^6$ is trifluoromethyl.

52. The compound of claim 51 which is 2,6-dichloro-N-(7-(trifluoromethyl)-3-benzisoxazolyl)-benzamide.

53. The compound of claim 49 wherein $R^6$ is chloro.

54. The compound of claim 53 which is 2,6-dichloro-N-(7-chloro-3-benzisoxazolyl)benzamide.

55. Method of suppressing insects of an order selected from the group consisting of Coleoptera, Diptera, Lepidoptera, and Orthoptera which comprises applying to the locus of the insects an effective amount of an active compound which is a compound of Claim 1.

56. The method of claim 55 wherein in the compound of claim 1 $R^2$ is a 3-isoxazolyl as recited in claim 1.

57. The method of claim 56 wherein in the compound of claim 1 $R^3$ is selected from the group consisting of
3-bromophenyl,
4-bromophenyl,
3-chlorophenyl,
4-chlorophenyl,
3-fluorophenyl,
4-fluorophenyl, or 3-4-dichlorophenyl.

58. The method of claim 57 wherein the active agent is 2,6-dichloro-N-(5-(3-bromophenyl)-3-isoxazolyl)benzamide.

59. The method of claim 57 wherein the active agent is 2,6-difluoro-N-(5-(3-bromophenyl)-3-isoxazolyl)-benzamide.

60. The method of claim 57 wherein the active agent is 2,6-dibromo-N-(5-(3-bromophenyl)-3-isoxazolyl)-benzamide.

61. The method of claim 57 wherein the active agent is 2,6-dichloro-N-(5-(4-bromophenyl)-3-isoxazolyl)-benzamide.

62. The method of claim 57 wherein the active agent is 2,6-dichloro-N-(5-(3-chlorophenyl)-3-isoxazolyl)-benzamide.

63. The method of claim 57 wherein the active agent is 2,6-dichloro-N-(5-(4-chlorophenyl)-3-isoxazolyl)-benzamide.

64. The method of claim 57 wherein the active agent is 2-chloro-N-(5-(4-chlorophenyl)-3-isoxazolyl)-benzamide.

65. The method of claim 57 wherein the active agent is 2,6-difluoro-N-(5-(4-chlorophenyl)-3-isoxazolyl)-benzamide.

66. The method of claim 57 wherein the active agent is 2,6-dibromo-N-(5-(4-chlorophenyl)-3-isoxazolyl)-benzamide.

67. The method of claim 57 wherein the active agent is 2-chloro-6-methyl-N-(5-(3-chlorophenyl)-3-isoxazolyl)benzamide.

68. The method of claim 57 wherein the active agent is 2,6-dichloro-N-(5-(3-fluorophenyl)-3-isoxazolyl)-benzamide.

69. The method of claim 57 wherein the active agent is 2,6-dichloro-N-(5-(4-fluorophenyl)-3-isoxazolyl)-benzamide.

70. The method of claim 57 wherein the active agent is 2,6-difluoro-N-(5-(4-fluorophenyl)-3-isoxazolyl)benzamide.

71. The method of claim 57 wherein the active agent is 2,6-dibromo-N-(5-(4-fluorophenyl)-3-isoxazolyl)-benzamide.

72. The method of claim 57 wherein the active agent is 2,6-dichloro-N-(5-(3,4-dichlorophenyl)-3-isoxazolyl)-benzamide.

73. The method of claim 55 wherein in the compound of claim 1 $R^1$ is methyl as recited in claim 1.

74. The method of claim 73 wherein the active agent is 2,6-difluoro-N-methyl-N-(5-(4-chlorophenyl)-3-isoxazolyl)benzamide.

75. The method of claim 73 wherein the active agent is a mixture of 2,6-dichloro-N-methyl-(5-(4-chlorophenyl)-3-isoxazolyl)benzamide and the endoalkylated or endo-acylated isoxazole tautomers thereof.

76. The method of claim 55 wherein in the compound of claim 1 $R^1$ is 2,6-dichlorobenzoyl as recited in claim 1.

77. The method of claim 76 wherein the active agent is 2,6-dichloro-N-2,6-dichlorobenzoyl-N-(5-(4-chlorophenyl)-3-isoxazolyl)benzamide.

78. The method of claim 56 wherein in the compound of claim 1 $R^3$ is selected from the group consisting of
4-tolyl,
3-(trifluoromethyl)phenyl,
4-(trifluoromethyl)phenyl,
3-phenoxy,
4-biphenylyl, or phenyl.

79. The method of claim 78 wherein the active agent is 2,6-dichloro-N-(5-(4-tolyl)-3-isoxazolyl)-benzamide.

80. The method of claim 78 wherein the active agent is 2,6-dichloro-N-(5-(3-(trifluoromethyl)phenyl)-3-isoxazolyl)benzamide.

81. The method of claim 78 wherein the active agent is 2-chloro-N-(5-(3-(trifluoromethyl)phenyl]-3-isoxazolyl)benzamide.

82. The method of claim 78 wherein the active agent is 2,6-difluoro-N-(5-(3-(trifluoromethyl)-phenyl)-3-isoxazolyl)benzamide.

83. The method of claim 78 wherein the active agent is 2,6-dibromo-N-(5-(3-(trifluoromethyl)-phenyl)-3-isoxazolyl)benzamide.

84. The method of claim 78 wherein the active agent is 2,6-dichloro-N-(5-(4-(trifluoromethyl)-phenyl)-3-isoxazolyl)benzamide.

85. The method of claim 78 wherein the active agent is 2,6-difluoro-N-(5-(4-(trifluoromethyl)-phenyl)-3-isoxazolyl)benzamide.

86. The method of claim 78 wherein the active agent is 2,6-dibromo-N-(5-(4-(trifluoromethyl)-phenyl)-3-isoxazolyl)benzamide.

87. The method of claim 78 wherein the active agent is 2,6-dichloro-N-(5-(3-(phenoxy)phenyl)-3-isoxazolyl)benzamide.

88. The method of claim 78 wherein the active agent is 2,6-dichloro-N-(5-(4-biphenylyl)-3-isoxazolyl)benzamide.

89. The method of claim 78 wherein the active agent is 2,6-difluoro-N-(5-(4-biphenylyl)-3-isoxazolyl)benzamide.

90. The method of claim 78 wherein the active agent is 2,6-dibromo-N-(5-(4-biphenylyl)-3-isoxazolyl)benzamide.

91. The method of claim 78 wherein the active agent is 2,6-dichloro-N-(5-phenyl-3-isoxazolyl)-benzamide.

92. The method of claim 55 wherein in the compound of claim 1 $R^2$ is a 5-isoxazolyl as recited in claim 1.

93. The method of claim 92 wherein in the compound of Claim 1 $R^5$ is selected from the group consisting of
hydrogen,
3-chlorophenyl,
4-chlorophenyl,
2-tolyl,
3-tolyl, or 3-(trifluoromethyl)phenyl.

94. The method of claim 93 wherein the active agent is 2,6-dimethoxy-N-(4-(4-(trifluoromethyl)-phenyl)-5-isoxazolyl)benzamide.

95. The method of claim 93 wherein the active agent is 2,6-dichloro-N-(3-(3-chlorophenyl)-5-isoxazolyl)benzamide.

96. The method of claim 93 wherein the active agent is 2,6-difluoro-N-(3-(3-chlorophenyl)-5-isoxazolyl)benzamide.

97. The method of claim 93 wherein the active agent is 2,6-dichloro-N-(3-(4-chlorophenyl)-5-isoxazolyl)benzamide.

98. The method of claim 93 wherein the active agent is 2,6-dimethyl-N-(3-(2-tolyl)-5-isoxazolyl)-benzamide.

99. The method of claim 93 wherein the active agent is 2,6-dimethoxy-N-(3-(2-tolyl)-5-isoxazolyl)benzamide.

100. The method of claim 93 wherein the active agent is 2,6-dimethoxy-N-(3-(3-tolyl)-5-isoxazolyl)benzamide.

101. The method of claim 93 wherein the active agent is 2,6-difluoro-N-(3-(3-tolyl)-5-isoxazolyl)-benzamide.

102. The method of claim 93 wherein the active agent is 2,6-difluoro-N-(3-(3-(trifluoromethyl)-phenyl)-5-isoxazolyl)benzamide.

103. The method of claim 55 wherein in the compound of claim 1 $R^2$ is a 3-benzisoxazolyl as recited in claim 1.

104. The method of claim 103 wherein the active agent is 2,6-dichloro-N-(3-benzisoxazolyl)benzamide.

105. The method of claim 103 wherein in the compound of claim 1 $R^6$ is trifluoromethyl.

106. The method of claim 105 wherein the active agent is 2,6-dichloro-N-(7-(trifluoromethyl)-3-benzisoxazolyl)benzamide.

107. The method of claim 103 wherein in the compound of claim 1 $R^6$ is chloro.

108. The method of claim 107 wherein the active agent is 2,6-dichloro-N-(7-chloro-3-benzisoxazolyl)benzamide.

109. Composition comprising an excipient and an insecticidally effective amount of an active agent which is a compound of claim 1.

110. The composition of claim 109 wherein in the compound of claim 1 $R^2$ is a 3-isoxazolyl as recited in claim 1.

111. The composition of claim 110 wherein in the compound of claim 1 $R^3$ is selected from the group consisting of
3-bromophenyl,
4-bromophenyl,
3-chlorophenyl,
4-chlorophenyl,
3-fluorophenyl,
4-fluorophenyl, or 3-4-dichlorophenyl.

112. The composition of claim 111 wherein the active agent is 2,6-dichloro-N-(5-(3-bromophenyl)-3-isoxazolyl)benzamide.

113. The composition of claim 111 wherein the active agent is 2,6-difluoro-N-(5-(3-bromophenyl)-3-isoxazolyl)benzamide.

114. The composition of claim 111 wherein the active agent is 2,6-dibromo-N-(5-(3-bromophenyl)-3-isoxazolyl)benzamide.

115. The composition of claim 111 wherein the active agent is 2,6-dichloro-N-(5-(4-bromophenyl)-3-isoxazolyl)benzamide.

116. The composition of claim 111 wherein the active agent is 2,6-dichloro-N-(5-(3-chlorophenyl)-3-isoxazolyl)benzamide.

117. The composition of claim 111 wherein the active agent is 2,6-dichloro-N-(5-(4-chlorophenyl)-3-isoxazolyl)benzamide.

118. The composition of claim 111 wherein the active agent is 2-chloro-N-(5-(4-chlorophenyl)-3-isoxazolyl)-benzamide.

119. The composition of claim 111 wherein the active agent is 2,6-difluoro-N-(5-(4-chlorophenyl)-3-isoxazolyl)benzamide.

120. The composition of claim 111 wherein the active agent is 2,6-dibromo-N-(5-(4-chlorophenyl)-3-isoxazolyl)benzamide.

121. The composition of claim 111 wherein the active agent is 2-chloro-6-methyl-N-(5-(3-chlorophenyl)-3-isoxazolyl)benzamide.

122. The composition of claim 111 wherein the active agent is 2,6-dichloro-N-(5-(3-fluorophenyl)-3-isoxazolyl)benzamide.

123. The composition of claim 111 wherein the active agent is 2,6-dichloro-N-(5-(4-fluorophenyl)-3-isoxazolyl)benzamide.

124. The composition of claim 111 wherein the active agent is 2,6-difluoro-N-(5-(4-fluorophenyl)-3-isoxazolyl)benzamide.

125. The composition of claim 111 wherein the active agent is 2,6-dibromo-N-(5-(4-fluorophenyl)-3-isoxazolyl)benzamide.

126. The composition of claim 111 wherein the active agent is 2,6-dichloro-N-(5-(3,4-dichlorophenyl)-3-isoxazolyl)benzamide.

127. The composition of claim 109 wherein in the compound of claim 1 $R^1$ is methyl as recited in claim 1.

128. The composition of claim 127 wherein the active agent is 2,6-difluoro-N-methyl-N-(5-(4-chlorophenyl)-3-isoxazolyl)benzamide.

129. The composition of claim 127 wherein the active agent is a mixture of 2,6-dichloro-N-methyl-(5-(4- chlorophenyl)-3-isoxazolyl)benzamide and the endo-alkylated or endo-acylated isoxazole tautomers thereof.

130. The composition of claim 109 wherein in the compound of claim 1 $R^1$ is 2,6-dichlorobenzoyl as recited in claim 1.

131. The composition of claim 130 wherein the active agent is 2,6-dichloro-N-2,6-dichlorobenzoyl-N-(5-(4-chlorophenyl)-3-isoxazolyl)benzamide.

132. The composition of claim 110 wherein in the compound of claim 1 $R^3$ is selected from the group consisting of
4-tolyl,
3-(trifluoromethyl)phenyl,
4-(trifluoromethyl)phenyl,
3-phenoxy,
4-biphenylyl, or phenyl.

133. The composition of claim 132 wherein the active agent is 2,6-dichloro-N-(5-(4-tolyl)-3-isoxazolyl)benzamide.

134. The composition of claim 132 wherein the active agent is 2,6-dichloro-N-(5-(3-(trifluoromethyl)phenyl)-3-isoxazolyl)benzamide.

135. The composition of claim 132 wherein the active agent is 2-chloro-N-(5-(3-(trifluoromethyl)-phenyl)-3-isoxazolyl)benzamide.

136. The composition of claim 132 wherein the active agent is 2,6-difluoro-N-(5-(3-(trifluoromethyl)phenyl)-3-isoxazolyl)benzamide.

137. The composition of claim 132 wherein the active agent is 2,6-dibromo-N-(5-(3-(trifluoromethyl)phenyl)-3-isoxazolyl)benzamide.

138. The composition of claim 132 wherein the active agent is 2,6-dichloro-N-(5-(4-(trifluoromethyl)phenyl-3-isoxazolyl)benzamide.

139. The composition of claim 132 wherein the active agent is 2,6-difluoro-N-(5-(4(trifluoromethyl)phenyl)-3-isoxazolyl)benzamide.

140. The composition of claim 132 wherein the active agent is 2,6-dibromo-N-(5-(4-(trifluoromethyl)phenyl)-3-isoxazolyl)benzamide.

141. The composition of claim 132 wherein the active agent is 2,6-dichloro-N-(5-(3-(phenoxy)-phenyl)-3-isoxazolyl)benzamide.

142. The composition of claim 132 wherein the active agent is 2,6-dichloro-N-(5-(4-biphenylyl)-3-isoxazolyl)-benzamide.

143. The composition of claim 132 wherein the active agent is 2,6-difluoro-N-(5-(4-biphenylyl)-3-isoxazolyl)-benzamide.

144. The composition of claim 132 wherein the active agent is 2,6-dibromo-N-(5-(4-biphenylyl)-3-isoxazolyl)-benzamide.

145. The composition of claim 132 wherein the active agent is 2,6-dichloro-N-(5-phenyl-3-isoxazolyl)benzamide.

146. The composition of claim 109 wherein in the compound of claim 1 $R^2$ is a 5-isoxazolyl as recited in claim 1.

147. The composition of claim 146 wherein in the compound of claim 1 $R^5$ is selected from the group consisting of
hydrogen,
3-chlorophenyl,
4-chlorophenyl,
2-tolyl,
3-tolyl, or 3-(trifluoromethyl)phenyl.

148. The composition of claim 147 wherein the active agent is 2,6-dimethoxy-N-(4-(4-(trifluoromethyl)-phenyl)-5-isoxazolyl)benzamide.

149. The composition of claim 147 wherein the active agent is 2,6-dichloro-N-(3-(3-chlorophenyl)-5-isoxazolyl)benzamide.

150. The composition of claim 147 wherein the active agent is 2,6-difluoro-N-(3-(3-chlorophenyl)-5-isoxazolyl)benzamide.

151. The composition of claim 147 wherein the active agent is 2,6-dichloro-N-(3-(4-chlorophenyl)-5-isoxazolyl)benzamide.

152. The composition of claim 147 wherein the active agent is 2,6-dimethyl-N-(3-(2-tolyl)-5-isoxazolyl)benzamide.

153. The composition of claim 147 wherein the active agent is 2,6-dimethoxy-N-(3-(2-tolyl)-5-isoxazolyl)benzamide.

154. The composition of claim 147 wherein the active agent is 2,6-dimethoxy-N-(3-(3-tolyl)-5-isoxazolyl)benzamide.

155. The composition of claim 147 wherein the active agent is 2,6-difluoro-N-(3-(3-tolyl)-5-isoxazolyl)benzamide.

156. The composition of claim 147 wherein the active agent is 2,6-dichloro-N-(3-(3-(trifluoromethyl)phenyl)-5-isoxazolyl)benzamide.

157. The composition of claim 109 wherein in the compound of claim 1 $R^2$ is a 3-benzisoxazolyl as recited in claim 1.

158. The composition of claim 157 wherein the active agent is 2,6-dichloro-N-(3-benzisoxazolyl)-benzamide.

159. The composition of claim 157 wherein in the compound of claim 1 $R^6$ is trifluoromethyl.

160. The composition of claim 159 wherein the active agent is 2,6-dichloro-N-(7-(trifluoromethyl)-3-benzisoxazolyl)benzamide.

161. The composition of claim 157 wherein in the compound of claim 1 $R^6$ is chloro.

162. The composition of claim 161 wherein the active agent is 2,6-dichloro-N-(7-chloro-3-benzisoxazolyl)benzamide.

* * * * *